US010722125B2

(12) United States Patent
Tal et al.

(10) Patent No.: US 10,722,125 B2
(45) Date of Patent: Jul. 28, 2020

(54) BLOOD PRESSURE SIGNAL ACQUISITION USING A PRESSURE SENSOR ARRAY

(71) Applicant: LIVEMETRIC (MEDICAL) S.A., Luxembourg (LU)

(72) Inventors: Nir Efraim Joseph Tal, Haifa (IL); Tomer Bentzion, Tel Aviv (IL)

(73) Assignee: LIVEMETRIC (MEDICAL) S.A., Luxembourg (LU)

( * ) Notice: Subject to any disclaimer, the term of this patent is extended or adjusted under 35 U.S.C. 154(b) by 754 days.

(21) Appl. No.: 15/401,432

(22) Filed: Jan. 9, 2017

(65) Prior Publication Data
US 2018/0116534 A1 May 3, 2018

Related U.S. Application Data

(60) Provisional application No. 62/415,003, filed on Oct. 31, 2016.

(51) Int. Cl.
*A61B 5/0205* (2006.01)
*A61B 5/021* (2006.01)
*A61B 5/00* (2006.01)

(52) U.S. Cl.
CPC ........ *A61B 5/02108* (2013.01); *A61B 5/0205* (2013.01); *A61B 5/681* (2013.01);
(Continued)

(58) Field of Classification Search
CPC ... A61B 5/02108; A61B 5/681; A61B 5/7203; A61B 5/7221; A61B 5/7267;
(Continued)

(56) References Cited

U.S. PATENT DOCUMENTS 4,605,010 A 8/1986 Mcewen
5,243,992 A 9/1993 Eckerle et al.
(Continued)

FOREIGN PATENT DOCUMENTS

JP 2011239840 12/2011
JP 2015501184 1/2015
(Continued)

OTHER PUBLICATIONS

Yousefi et al., "Adaptive Cancellation of Motion Artifacts in Waerable Biosensors", 34 Conf. IEEE EMBS, pp. 2004-2208, Aug. 28, 2012.
(Continued)

*Primary Examiner* — Navin Natnithithadha
(74) *Attorney, Agent, or Firm* — The Roy Gross Law Firm, LLC; Roy Gross

(57) ABSTRACT

A system and method for blood pressure signal acquisition using a pressure sensor array. A solution is provided for a non-inflatable, non-invasive, continuous blood pressure waveform and blood pressure acquisition system. The system is operative to combine signals from various sensing elements where the less accurate sensor elements are calibrated utilizing the more accurate sensor elements. Blood pressure measurements are acquired using very sensitive pressure sensors that detect slight pressure changes through the skin, which are sampled and processed to yield a blood pressure signal, which is processed to yield actual systolic and diastolic continuous and or intermittent blood pressure readings. By sampling and detecting the signal in each of the sensors, the sensor that is best placed on the target artery is found and the signals from that sensor is used to weight the signals from other sensors based on signal quality. The sensor array is placed approximately on the target artery making it highly likely that more than one element will
(Continued)

acquire signal from the artery. Combining a plurality of such correlated signals with uncorrelated noise yields a signal to noise enhancement and more accurate blood pressure readings.

28 Claims, 12 Drawing Sheets

(52) U.S. Cl.
CPC .......... *A61B 5/7203* (2013.01); *A61B 5/7221* (2013.01); *A61B 5/7225* (2013.01); *A61B 5/7267* (2013.01); *A61B 2560/0209* (2013.01); *A61B 2560/0223* (2013.01); *A61B 2562/0247* (2013.01); *A61B 2562/04* (2013.01); *A61B 2562/043* (2013.01)

(58) Field of Classification Search
CPC .... A61B 2560/0209; A61B 2560/0223; A61B 2562/0247; A61B 2562/043
USPC ................ 600/481, 483–486, 488, 490–499
See application file for complete search history.

(56) References Cited

U.S. PATENT DOCUMENTS

| | | | |
|---|---|---|---|
| 7,395,105 | B2 | 7/2008 | Schmidt et al. |
| 7,438,687 | B2 | 10/2008 | Lewicke |
| 7,539,532 | B2 | 5/2009 | Tran |
| 7,641,614 | B2 | 1/2010 | Asada et al. |
| 8,747,327 | B2 | 6/2014 | Kim et al. |
| 9,149,230 | B2 | 10/2015 | Caron et al. |
| 9,398,880 | B2 | 7/2016 | Barnett |
| 9,504,392 | B2 | 11/2016 | Caron et al. |
| 2006/0036185 | A1 | 2/2006 | Lewicke et al. |
| 2007/0055163 | A1 | 3/2007 | Asada et al. |
| 2007/0265533 | A1 | 11/2007 | Tran |
| 2008/0228089 | A1 | 9/2008 | Cho et al. |
| 2010/0286538 | A1 | 11/2010 | Kim et al. |
| 2011/0112379 | A1 | 5/2011 | Li et al. |
| 2011/0152700 | A1 | 6/2011 | Sawanoi et al. |
| 2011/0166461 | A1 | 7/2011 | Susstrunk et al. |
| 2012/0053424 | A1 | 3/2012 | Kenalty et al. |
| 2013/0275057 | A1 | 10/2013 | Perlin et al. |
| 2014/0081160 | A1 | 3/2014 | Xiang |
| 2014/0243709 | A1 | 8/2014 | Gibson et al. |
| 2014/0249386 | A1 | 9/2014 | Caron et al. |
| 2014/0288383 | A1 | 9/2014 | Barnett |
| 2014/0288443 | A1 | 9/2014 | Meriheina et al. |
| 2014/0288445 | A1 | 9/2014 | Makkonen et al. |
| 2014/0330145 | A1 | 11/2014 | Brodnick |
| 2015/0366518 | A1 | 12/2015 | Sampson |
| 2015/0370398 | A1 | 12/2015 | Perlin et al. |
| 2016/0066894 | A1 | 3/2016 | Barton-sweeney |
| 2016/0094899 | A1 | 3/2016 | Aumer et al. |
| 2016/0113517 | A1 | 4/2016 | Lee et al. |
| 2016/0262695 | A1 | 9/2016 | Zhang et al. |
| 2016/0287110 | A1 | 10/2016 | Morris et al. |
| 2016/0338602 | A1* | 11/2016 | Oksala ............... A61B 5/02125 |
| 2016/0367406 | A1 | 12/2016 | Barnett |
| 2017/0360306 | A1 | 12/2017 | Narasimhan et al. |
| 2018/0325454 | A1 | 11/2018 | Petelenz et al. |

FOREIGN PATENT DOCUMENTS

| | | |
|---|---|---|
| JP | 5561674 B2 | 7/2017 |
| WO | WO 2005/094672 A1 | 10/2005 |
| WO | WO 2006/020956 A2 | 2/2006 |
| WO | WO 2006/094107 A1 | 9/2006 |
| WO | WO 2007/024777 A2 | 3/2007 |
| WO | WO 2009/125349 A2 | 10/2009 |
| WO | WO 2013/061281 A1 | 5/2013 |
| WO | WO 2014/153399 A1 | 9/2014 |
| WO | WO 2015/107269 A1 | 7/2015 |
| WO | WO 2015/143259 A1 | 9/2015 |
| WO | WO 2015/172897 A1 | 11/2015 |
| WO | WO 2015/183470 A9 | 12/2015 |
| WO | WO 2016/040253 A1 | 3/2016 |
| WO | WO 2016/040256 A1 | 3/2016 |
| WO | WO 2016/041073 A1 | 3/2016 |
| WO | WO 2016/061668 A1 | 4/2016 |
| WO | WO 2016/065463 A1 | 5/2016 |
| WO | WO 2016/065476 A1 | 5/2016 |
| WO | WO 2016/161227 A2 | 10/2016 |
| WO | WO 2017/074713 A1 | 5/2017 |
| WO | WO 2018/081208 A1 | 5/2018 |

OTHER PUBLICATIONS

Valle-Lopera et al., "Test and fabrication of piezoresistive sensors for contact pressure measurement", Revista Facultad de Ingeniería, Univ Antigua, No. 82, pp. 47-52, 2017.
International Search Report issued in PCT/US2016/056958 dated Jan. 26, 2017.
International Search Report issued in PCT/US2017/058197 dated Mar. 1, 2018.
International Search Report issued in PCT/US2017/058419 dated Apr. 12, 2018.
International Search Report issued in PCT/US2017/058420 dated Apr. 12, 2018.
Written Opinion issued in PCT/US2016/056958 dated Jan. 26, 2017.
Written Opinion issued in PCT/US2017/058197 dated Mar. 1, 2018.
Written Opinion issued in PCT/US2017/058419 dated Apr. 12, 2018.
Written Opinion issued in PCT/US2017/058420 dated Apr. 12, 2018.
Connell et al., "Continuous Wearable Blood Pressure Monitor", Medical Design Briefs, p. 22, Nov. 2016.

\* cited by examiner

BLOOD PRESSURE SIGNAL ACQUISITION USING A PRESSURE SENSOR ARRAY

REFERENCE TO PRIORITY APPLICATION

This application claims priority to U.S. Provisional Application Ser. No. 62/415,003, filed Oct. 31, 2016, entitled "A Method and Apparatus for Measuring Blood Pressure Using a Sensor Array," incorporated herein by reference in its entirety.

FIELD OF THE DISCLOSURE

The subject matter disclosed herein relates to the field of monitoring vital signs of a user and more particularly relates to a system and method for blood pressure signal acquisition using a pressure sensor array.

BACKGROUND OF THE INVENTION

High blood pressure is a common condition in which the long-term force of the blood against your artery walls is high enough that it may eventually cause health problems, such as heart disease. Blood pressure is determined both by the amount of blood your heart pumps and the amount of resistance to blood flow in your arteries. The more blood your heart pumps and the narrower your arteries, the higher your blood pressure.

One can have high blood pressure (i.e. hypertension) for years without any symptoms. Even without symptoms, damage to blood vessels and one's heart continues and can be detected. Uncontrolled high blood pressure increases one's risk of serious health problems, including heart attack and stroke. High blood pressure generally develops over many years, and it affects nearly everyone eventually. Fortunately, high blood pressure can be easily detected.

Currently, cardiovascular diseases represent a large proportion of all reported deaths globally. These diseases are considered a severe and shared risk, with a majority of the burden in low and middle income countries. A major factor that increases the risk of heart failures or strokes, speeds up hardening of blood vessels and reduces life expectancy is hypertension or high blood pressure.

Hypertension is a chronic health condition in which the pressure exerted by the circulating blood upon the walls of blood vessels is elevated. In order to ensure appropriate circulation of blood in blood vessels, the heart of a hypertensive person must work harder than normal, which increases the risk of heart attack, stroke and cardiac failure. Eating a healthy diet and exercising, however, can significantly improve blood pressure control and decrease the risk of complications. Efficient drug treatments are also available. It is therefore important to find persons with elevated blood pressures and monitor their blood pressure information on a regular basis.

During each heartbeat, the blood pressure varies between a maximum (i.e. systolic) and a minimum (i.e. diastolic) pressure. A traditional noninvasive way to measure blood pressure has been to use a pressurized cuff and detect the pressure levels where the blood flow starts to pulsate (i.e. cuff pressure is between the systolic and diastolic pressure) and where there is no flow at all (i.e. cuff pressure exceeds systolic pressure). It has been seen, however, that users tend to consider the measurement situations, as well as the pressurized cuff tedious and even stressing, especially in long-term monitoring. In addition, the well-known white-coat syndrome tends to elevate the blood pressure during the measurement which leads to inaccurate diagnoses.

The use of wearable devices for monitoring body physiological parameters (e.g. blood pressure, heart rate (HR) pulse, body temperature, blood glucose level, movement patterns, etc.) noninvasively, continuously and/or intermittently for extended periods of time are becoming popular as a way to monitor and improve health.

Traditional blood pressure measurements require inflatable cuffs, which are gradually deflated from a state of full vessel occlusion to a lower pressure while listening using a mechanical sensor (e.g., stethoscope) to the sounds generated by the blood flow eddies in the vessel. An advantage of this method is its relative robustness to movements, while a disadvantage is its large form factor and the need for either manual inflation by the user or an automatic pump, which requires large quantities of energy. Since energy efficiency and small form factor are major requirements in wearable devices, inflatable cuff blood pressure sensing is not a useful paradigm in this space.

Prior art blood pressure measurement devices have significant disadvantages. First, the positioning or placement of the sensor on the radial artery is challenging to the user. Second, the sensor typically requires calibration in order to obtain correct readings. Third, the signal to noise ratio (SNR) obtained from the sensor might not be sufficient to obtain reliable blood pressure readings.

There is thus a need for a mechanism capable of continuously measuring and monitoring blood pressure that overcomes the disadvantages of traditional prior art devices and methods. For example, the mechanism of measuring blood pressure should not require the use of an inflatable cuff with its associated high energy requirements. In addition, the mechanism should be able to sense the blood pressure waveform on one or more of the arteries in the arm (i.e. the radial and ulnar arteries) while significantly reducing or eliminating motion artifacts from the waveform.

SUMMARY OF THE INVENTION

The present invention is a system and method for blood pressure signal acquisition using a based pressure sensor array. A solution is provided for a non-inflatable, non-invasive, continuous blood pressure waveform and blood pressure acquisition system. The system is operative to combine signals from various sensing elements where the less accurate sensor elements are calibrated utilizing the more accurate sensor elements.

One technique to acquire blood pressure is to use very sensitive pressure sensors implemented using sensitive pressure sensors, which could be implemented, for example, in Micro Electrical-Mechanical Systems (MEMS) by capacitive or resistive sensing means. Such a sensor carefully placed on the radial or ulnar artery can detect slight pressure changes through the skin, which, if carefully sampled and processed can yield a blood pressure signal, which can in turn be processed to yield actual systolic and diastolic continuous and or intermittent blood pressure readings.

The invention overcomes three key technological barriers of such a system: (1) how to accurately place the sensor on the target artery; (2) how to calibrate the sensors; and (3) how to improve the signal to noise ratio of the blood pressure waveform.

Regarding sensor placement, the diameter of a typical radial artery is only a few millimeters. Aligning a sensor pressure sensor, such that it is perpendicular and touching the skin over the radial artery can be challenging, especially in the context of a wearable device. The invention overcomes this difficulty by providing an array of sensors, e.g., linear, two dimensional, etc., whereby the sensors cover sufficient area of the wrist so that it is highly likely that at least one sensor will be optimally or close to optimally located on the radial or ulnar arteries.

Regarding sensor calibration, due to the extreme dependence of capacitive MEMS pressure sensors on temperature, batch and other parameters, they are inherently not suitable for measuring absolute pressure with mmHg accuracy without calibration. The invention overcomes this difficulty by including both capacitive (i.e. lower accuracy) and resistive (i.e. high accuracy) sensors in the sensor array. The more accurate resistive type sensors are used to calibrate the less accurate capacitive type sensors.

Regarding signal to noise ratio (SNR), since the blood pressure measurements are required to have good signal to noise ratio, and the actual signal sensed is a transmitted pressure waveform through the vessel boundaries and skin tissue there is a significant attenuation leading to reduced signal to noise ratio. This coupled with the intrapatient physiology changes makes it very difficult to sense the pressure wave consistently. The invention overcomes this difficulty by providing techniques to improve the SNR of the sensor data. A composite blood pressure waveform is generated by estimating and applying scale factors (i.e. weights) to the sensor data. The scaled data is summed and a composite waveform is output. Alternatively, the data from all sensors is read and one or more quality metrics are computed and the sensor data corresponding to the leading metric is selected for further processing while discarding data from the non-selected sensors.

Thus, the system and method of the present invention provides a compact family of sensor elements that alleviates all three design concerns described supra. Due to the multiple sensors, several sensor types can be used, which can calibrate the less accurate sensors, i.e. capacitive pressure MEMS sensors or force sensitive resistor (FSR) devices.

In addition, because the system can sample and detect the signal in each one of the sensors, it can detect which sensor is best placed on the target artery and use the signals from that sensor or to weight the signals from the various elements based on signal quality.

Furthermore, since the sensor array is placed approximately on the target artery, it is highly likely that more than one element will acquire signal from the artery. Combining a plurality of such correlated signals with uncorrelated noise will yield signal to noise enhancement yielding much more accurate blood pressure readings.

There is thus provided in accordance with the invention, a method of obtaining an output blood pressure (BP) signal, comprising providing a plurality of N pressure sensors, acquiring a plurality of N blood pressure waveform signals, each waveform signal acquired from one of the pressure sensors, and combining the N blood pressure waveform signals to generate the output blood pressure signal therefrom.

There is also provided in accordance with the invention, a method of obtaining an output blood pressure (BP) signal, comprising providing a plurality of N pressure sensors, acquiring a plurality of N blood pressure waveform signals, each waveform signal acquired from one of the pressure sensors, and selecting one of the N blood pressure waveform signals in accordance with one or more quality metrics as the output blood pressure signal.

There is further provided in accordance with the invention, a method of obtaining an output blood pressure (BP) signal, comprising providing a plurality of N pressure sensors, acquiring a plurality of N blood pressure waveform signals, each waveform signal acquired from one of the pressure sensors, utilizing waveform signals from one or more relatively accurate pressure sensors from among the plurality of pressure sensors to calibrate one or more less accurate pressure sensors within the plurality of pressure sensors, and combining the N blood pressure waveform signals including one or more calibrated blood pressure waveform signals to generate the composite output blood pressure signal therefrom.

There is also provided in accordance with the invention, a method of obtaining an output blood pressure (BP) signal, comprising providing a plurality of N pressure sensors, acquiring a plurality of N blood pressure waveform signals, each waveform signal acquired from one of the pressure sensors, utilizing waveform signals from one or more relatively accurate pressure sensors from among the plurality of pressure sensors to calibrate one or more less accurate pressure sensors within the plurality of pressure sensors, and selecting one of the N blood pressure waveform signals in accordance with one or more metrics and outputting the selected signal as the output blood pressure signal.

There is further provided in accordance with the invention, an apparatus for obtaining an output blood pressure (BP) signal, comprising a plurality of N pressure sensors, an acquisition circuit operative to acquire a plurality of N blood pressure waveform signals, each waveform signal derived from one of the pressure sensors, and a processor, the processor programmed to combine the N blood pressure waveform signals to generate the output blood pressure signal therefrom.

There is also provided in accordance with the invention, an apparatus for obtaining an output blood pressure (BP) signal, comprising a plurality of N pressure sensors, an acquisition circuit operative to acquire a plurality of N blood pressure waveform signals, each waveform signal from one of the pressure sensors, a processor, the processor programmed to utilize waveform signals from one or more relatively accurate pressure sensors from among the plurality of pressure sensors to calibrate one or more less accurate pressure sensors within the plurality of pressure sensors, and combining the N blood pressure waveform signals including one or more calibrated blood pressure waveform signals to generate the composite output blood pressure signal therefrom.

There is further provided in accordance with the invention, an apparatus for obtaining an output blood pressure (BP) signal, comprising a plurality of N pressure sensors, an acquisition circuit operative to acquire a plurality of N blood pressure waveform signals, each waveform signal acquired from one of the pressure sensors, a processor, the processor programmed to utilize waveform signals from one or more relatively accurate pressure sensors from among the plurality of pressure sensors to calibrate one or more less accurate pressure sensors within the plurality of pressure sensors, and select one of the N blood pressure waveform signals in accordance with one or more quality metrics, output the selected signal as the output blood pressure signal.

BRIEF DESCRIPTION OF THE DRAWINGS

The invention is herein described, by way of example only, with reference to the accompanying drawings, wherein.

DETAILED DESCRIPTION

Figure 1:
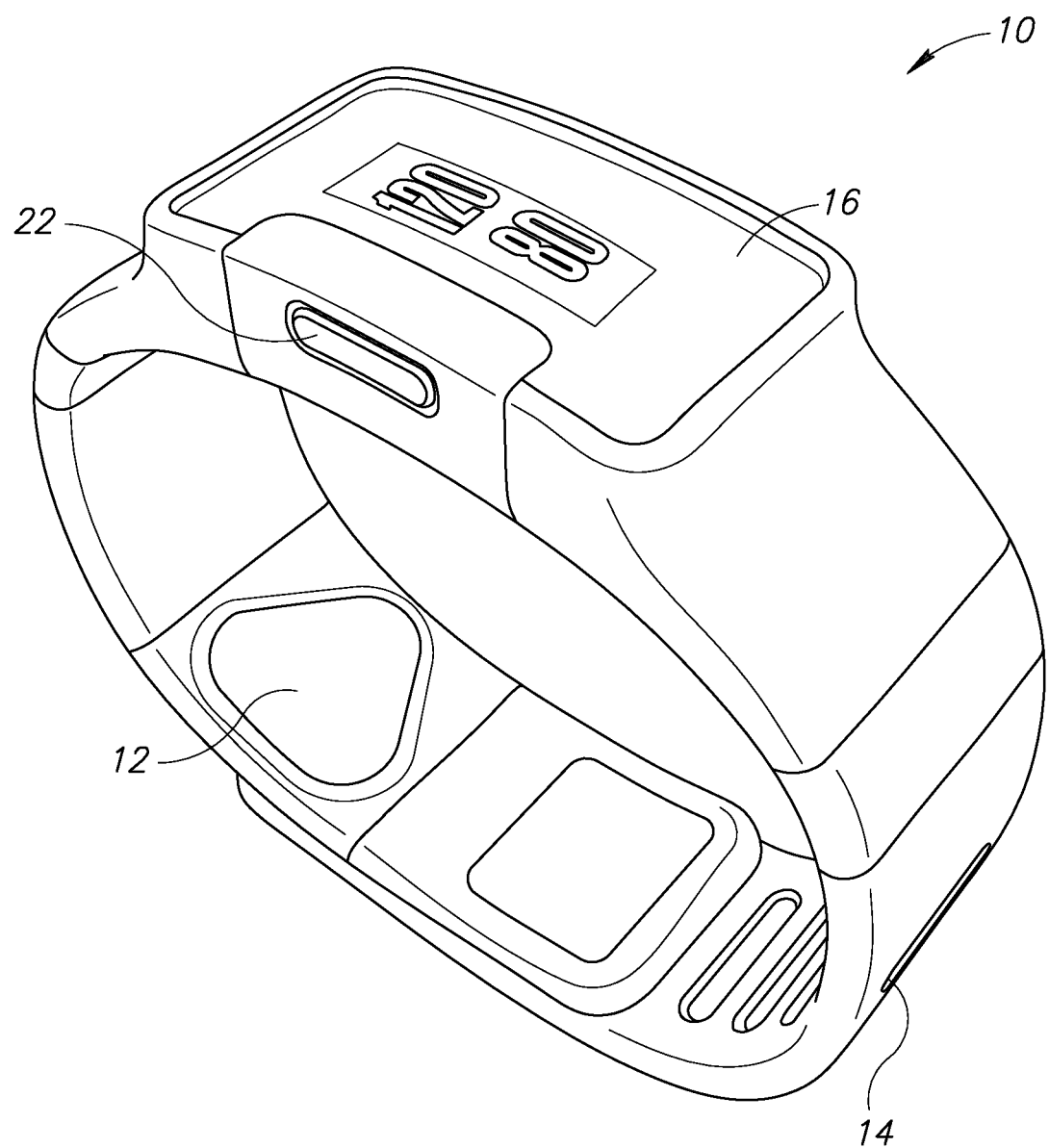
FIG. 1 is a diagram illustrating a first view of an example wearable device of the present invention operative to measure a user's blood pressure.

In the following detailed description, numerous specific details are set forth in order to provide a thorough understanding of the invention. It will be understood by those skilled in the art, however, that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary, for the understanding and appreciation of the underlying concepts of the present invention and in order not to obfuscate or distract from the teachings of the present invention.

Any reference in the specification to a method should be applied mutatis mutandis to a system capable of executing the method. Any reference in the specification to a system should be applied mutatis mutandis to a method that may be executed by the system.

As will be appreciated by one skilled in the art, the present invention may be embodied as a system, method, computer program product or a combination thereof. Accordingly, the present invention may take the form of a hardware embodiment, a software embodiment (including firmware, resident software, micro-code, etc.) or an embodiment combining software and hardware aspects that may all generally be referred to herein as a "circuit," "module" or "system." Furthermore, portions of the present invention may take the form of a computer program product embodied in any tangible medium of expression having computer usable program code embodied in the medium.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain or store the program for use by or in connection with the instruction execution system, apparatus, or device.

Computer program code for carrying out operations of the present invention may be written in any combination of one or more programming languages, including an object-oriented programming language such as Java, Smalltalk, C++, C# or the like, conventional procedural programming languages, such as the "C" programming language, and functional programming languages such as Prolog and Lisp, machine code, assembler or any other suitable programming languages. The program code may execute entirely or partly on the wearable device, on a host device, and/or in the cloud. In the latter scenario, wearable device, host, and/or cloud may be connected through any type of network using any type of network protocol, including for example a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented or supported by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

The invention is operational with numerous general purpose or special purpose computing system environments or configurations. Examples of well-known computing systems, environments, and/or configurations that may be suitable for use with the invention including wearable device processor, host device and cloud, include, but are not limited to, personal computers, server computers, cloud computing, hand-held or laptop devices, multiprocessor systems, microprocessor, microcontroller or microcomputer based systems, set top boxes, programmable consumer electronics, ASIC or FPGA core, DSP core, network PCs, minicomputers, mainframe computers, distributed computing environments that include any of the above systems or devices, and the like.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or by combinations of special purpose hardware and computer instructions.

Figure 2:
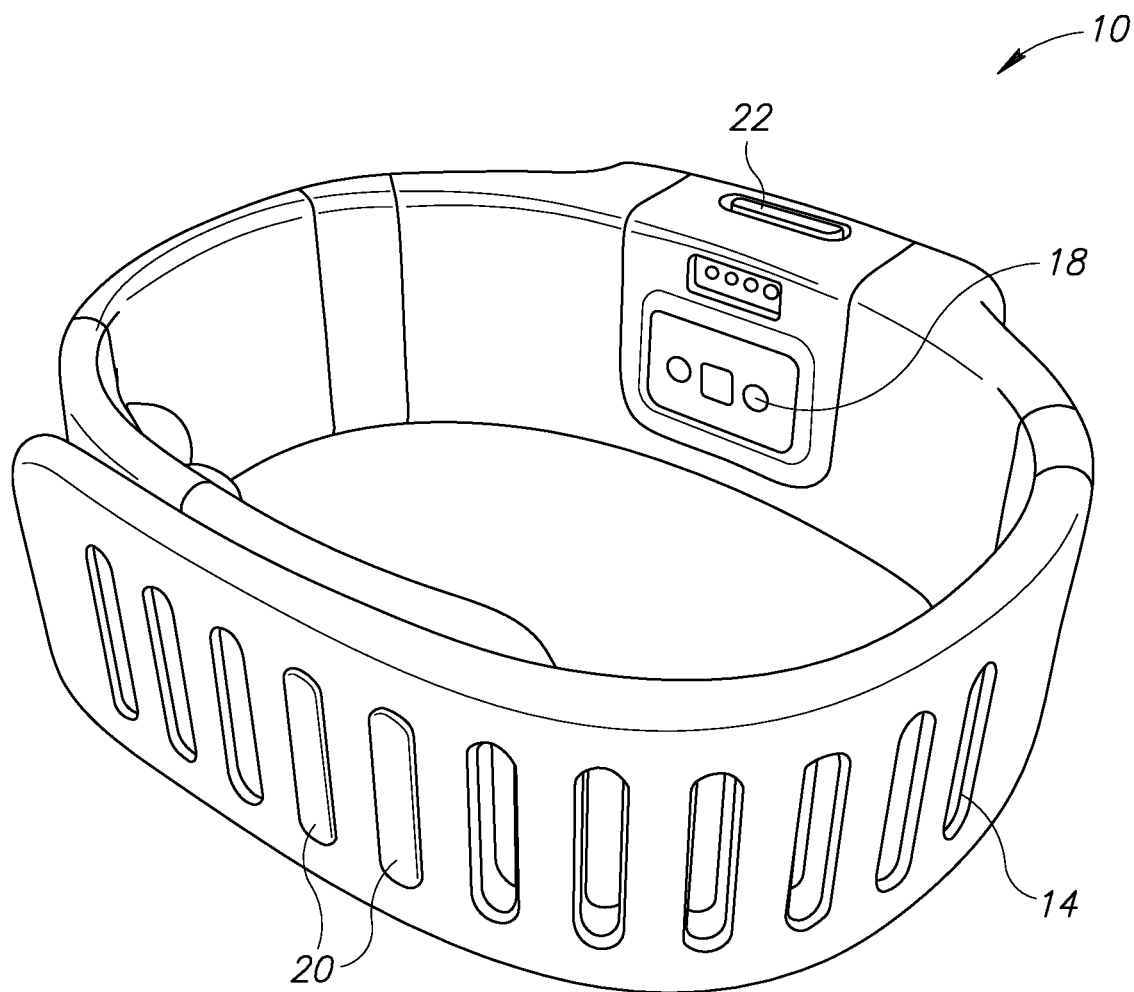
FIG. 2 is a diagram illustrating a second view of an example wearable device of the present invention operative to measure a user's blood pressure.

A diagram illustrating a first view of an example wearable device of the present invention operative to measure a user's blood pressure is shown in FIG. 1. A diagram illustrating a second view of an example wearable device of the present invention operative to measure a user's blood pressure is shown in FIG. 2. The wearable device, generally referenced 10, comprises a display 16 (e.g., viewable OLED, etc.) mounted in a housing containing a CPU, memory, wired and wireless communications, etc., one or more buttons 22, wrist band 14 housing a pressure sensor array 12, one or more optical or other non-pressure sensors 18 and strap closure, holding or lock mechanism 20. The wrist band strap has an embedded pressure sensor on it and is intended to be closed against the wrist whilst applying sensor array 12 on at least one of the radial, ulnar and brachial arteries and apply medium pressure thereon (i.e. significantly less than the systolic pressure but enough to sense the pressure wave).

Figure 3A:
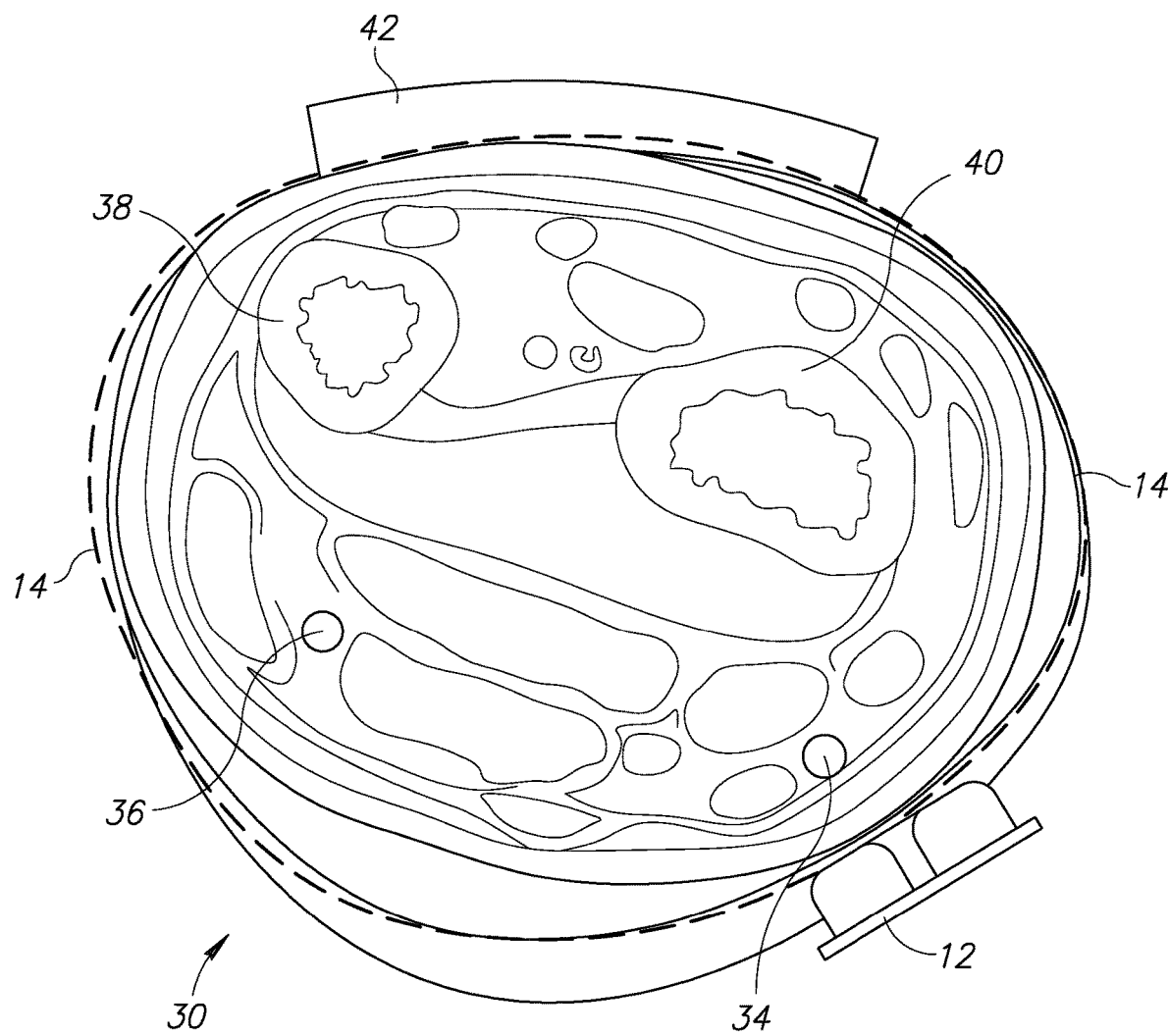
FIG. 3A is a diagram illustrating a cross section of a user's wrist showing the orientation of the blood vessels, pressure sensors and device housing.

A diagram illustrating a cross section (i.e. transverse section) of the left-hand wrist with the hand facing inward, generally referenced 30, of a user's wrist showing the orientation of the blood vessels, pressure sensors and device housing is shown in FIG. 3A. The main housing 42 of the wearable is positioned at the top of the wrist with the strap 14 placed around the wrist. The cross section shows the radius 40 and ulna bones 38; and radial 34 and ulnar 36 arteries of the arm. In this example, the pressure sensor array 12 is placed in the area of the wrist where the radial artery 34 is located.

Figure 3B:
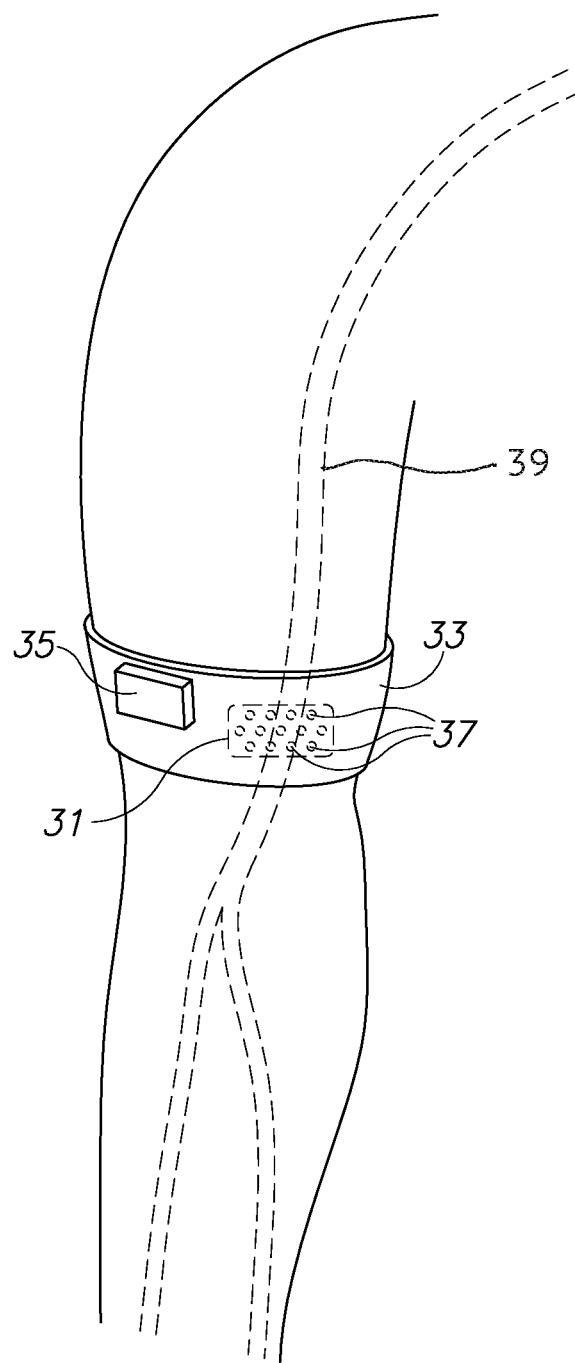
FIG. 3B is a diagram illustrating an example wearable device of the present invention adapted to be placed on the arm and operative to measure a user's blood pressure.

A diagram illustrating an example wearable device of the present invention adapted to be placed on the arm and operative to measure a user's blood pressure is shown in FIG. 3B. In an alternative embodiment, the wearable device is configured to be placed on a user's arm above or below the elbow. The wearable device comprises an arm band 33, sensor array 31 including a plurality of sensor elements 37, and housing 35 which contains electronics, display, buttons, etc.

In operation, the sensor array 31 is located on the bottom portion of the arm band and shown in dashed lines is placed over the brachial artery 39 before it forks into the radial and ulnar arteries. Alternatively, the sensor array and arm band may be placed on the arm below the elbow where it senses blood pressure from the radial or ulnar artery. The device may comprise a communications system whereby blood pressure data is relayed to an external host device which is operative to process the signal data and generate blood pressure measurements therefrom. Alternatively, the device may comprise a suitably programmed processor adapted to process the sensor signal data itself and generate continuous blood pressure measurements. In another embodiment, the device may be configured to operate in combination with a wrist worn device as described supra whereby the arm band device communicates wirelessly with the wrist worn device. For example, raw sensor signal data may be communicated wirelessly from the arm band device to the wrist worn device where it is processed and a blood pressure measurements are displayed to the user on the wrist worn device.

It is noted that the pressure sensor array may comprise numerous different configurations. The invention is not limited to any one configuration as numerous configurations are contemplated. Several example configurations will now be presented.

Figure 4A:
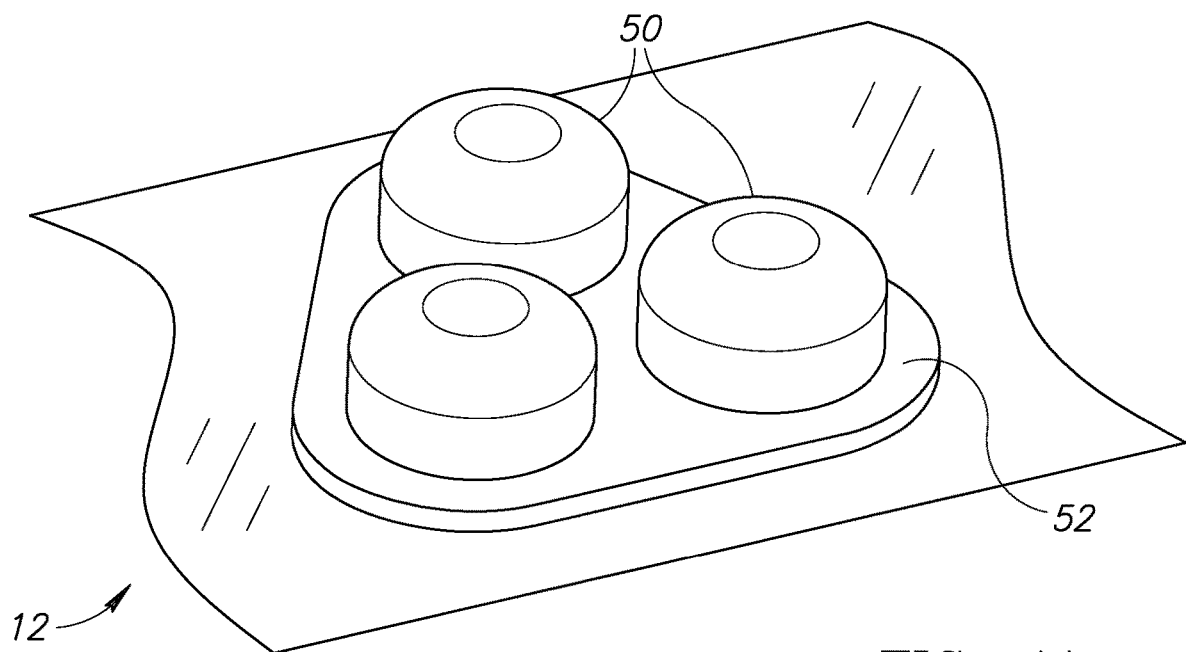
FIG. 4A is a diagram illustrating a first embodiment of an example blood pressure sensor array of the present invention.

A diagram illustrating a first embodiment of an example blood pressure sensor array of the present invention is shown in FIG. 4A. In this example, the sensor array 12 comprises three pressure sensors. The three sensors are configured on the wrist strap such then when placed to a user's wrist, they will be positioned approximately on the radial artery. The device is configured to receive signals from all three sensors simultaneously. One of the signals may be selected as the blood pressure waveform for further processing or a composite signal made up of a weighted sum of all the signals may be used to generate the blood pressure waveform.

It is important to note that acquiring multiple signals from a plurality of pressure sensors eliminates the problem of correct placement of the pressure sensor array. As long as at least one of the pressure sensors is placed correctly or correctly enough, the signal received may be sufficient to derive correct blood pressure readings from the blood pressure waveform.

Figure 4B:
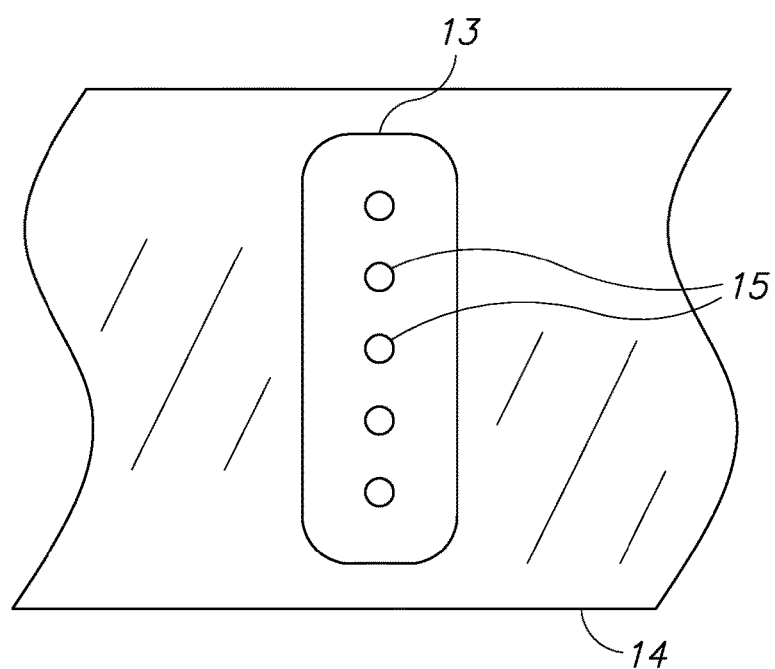
FIG. 4B is a diagram illustrating a second embodiment of an example blood pressure sensor array of the present invention.

A diagram illustrating a second embodiment of an example blood pressure sensor array of the present invention is shown in FIG. 4B. In this example, the pressure sensor array 13 on the wrist band 14 comprises a plurality of sensors 15 configured in a linear array. The device is configured to receive signals from all sensors simultaneously. One of the signals may be selected as the blood pressure waveform for further processing or a composite signal made up of a weighted sum of all the signals may be used to generate the blood pressure waveform. Acquiring multiple signals from a plurality of pressure sensors arranged in a linear array eliminates the problem of correct placement of the pressure sensor array. As long as at least one of the pressure sensors is placed correctly or correctly enough, the signal received may be sufficient to derive correct blood pressure readings from the blood pressure waveform. It is appreciated that the linear array of sensors may be configured perpendicular to the wrist strap as shown in FIG. 4B or may be configured at any desired angle with reference to the wrist strap.

Figure 4C:
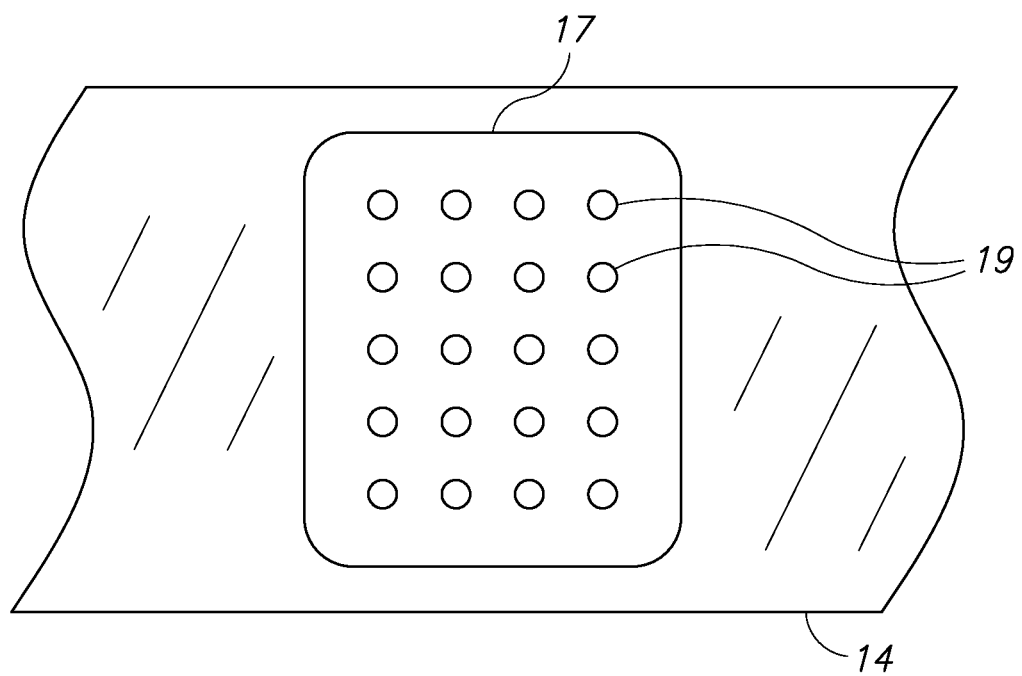
FIG. 4C is a diagram illustrating a third embodiment of an example blood pressure sensor array of the present invention.

A diagram illustrating a third embodiment of an example blood pressure sensor array of the present invention is shown in FIG. 4C. In this example, the pressure sensor array 17 on the wrist band 14 comprises a plurality of sensors 19 configured in a two dimensional (2D) array. The device is configured to receive signals from all sensors simultaneously. One of the signals may be selected as the blood pressure waveform for further processing or a composite signal made up of a weighted sum of all the signals may be used to generate the blood pressure waveform. Acquiring multiple signals from a plurality of pressure sensors arranged in a 2D array eliminates the problem of correct placement of the pressure sensor array. As long as at least one of the pressure sensors is placed correctly or correctly enough, the signal received may be sufficient to derive correct blood pressure readings from the blood pressure waveform. It is appreciated that the 2D array of sensors may be configured perpendicular to the wrist strap as shown in FIG. 4B or may be configured at any desired angle with reference to the wrist strap.

Figure 5:
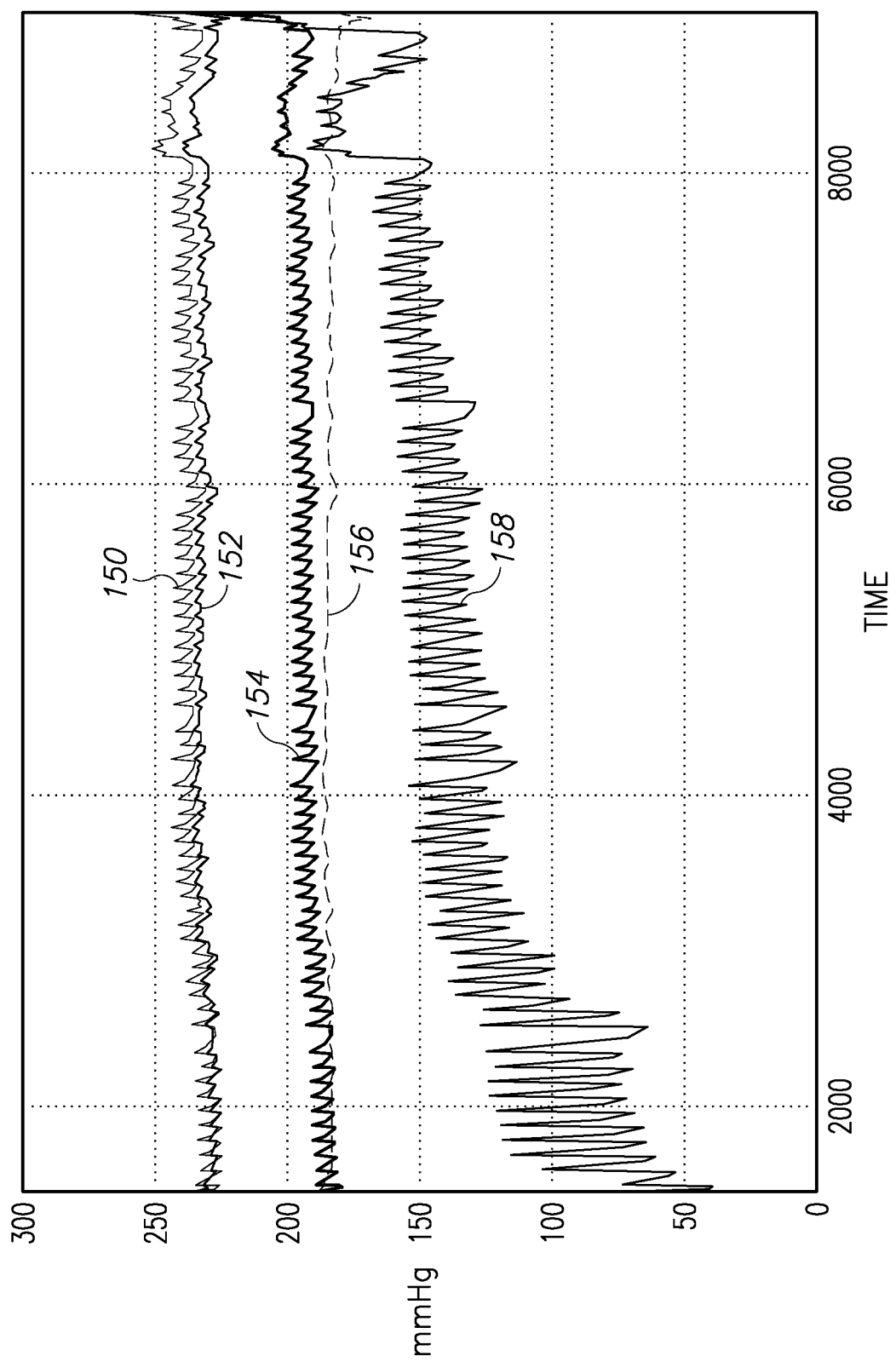
FIG. 5 is a diagram illustrating multiple traces representing signals output of a plurality of pressure sensors, each sensor having a different location on a user's wrist.

A diagram illustrating multiple traces representing signals output of a plurality of pressure sensors, each sensor having a different location on a user's wrist is shown in FIG. 5. The five traces shown, namely traces 150, 152, 154, 156, 158 represent output signals from five different pressure sensors configured in a sensor array, such as described supra, and placed on a user's wrist. The x-axis represents time while the y-axis represents mmHg which is related to the amplitude of the sensor output signal.

As expected, some of the signals are of higher quality than others. In particular, signals in traces 152 and 156 barely pick up any signal and are very weak indicating they are not in position to pick up pressure from the radial artery. Signals in traces 150 and 154 pick up stronger signals are but still fairly weak indicating they are also not in position on the radial artery. The signal in trace 158, however, is relatively strong indicating it is well placed on the radial artery and can be used as the blood pressure waveform for subsequent processing. It is appreciated that although five pressure sensor signals were shown in this example, any number of two or more sensors may be used without departing from the scope of the invention.

In another embodiment, the individual pressure sensors making up an array may comprise different types of sensors. For example, a first portion of the sensors may comprise capacitive pressure sensors which typically have low power consumption and low accuracy. A second portion of the sensors may comprise resistive pressure sensors which typically have high power consumption but better accuracy. In one embodiment, the signal obtained from one or more of the resistive pressure sensors (i.e. relatively higher accuracy sensors) is used to calibrate the readings from the one or more capacitive pressure sensors (i.e. relatively lower accuracy sensors), thereby yielding a blood pressure reading having significantly higher accuracy.

In one embodiment, the signal from one of the pressure sensors in the array is selected as the blood pressure waveform used to derive blood pressure readings from. The signals from all other non-selected sensors is ignored or discarded. The sensor signals may be analyzed for any desired one or more quality metrics, e.g., SNR, RSSI, etc.

In another embodiment, signals from all or a portion of the pressure sensors in the array are combined using a weighting scheme to generate a composite blood pressure waveform having an improved signal to noise ratio (SNR). The composite blood pressure waveform is then used to generate a more accurate blood pressure reading.

In another embodiment, the two techniques described supra, may be combined where one or more sensor signals are selected based on any desired quality metric and these signals are weighted and combined to generate a composite blood pressure waveform.

Figure 6:
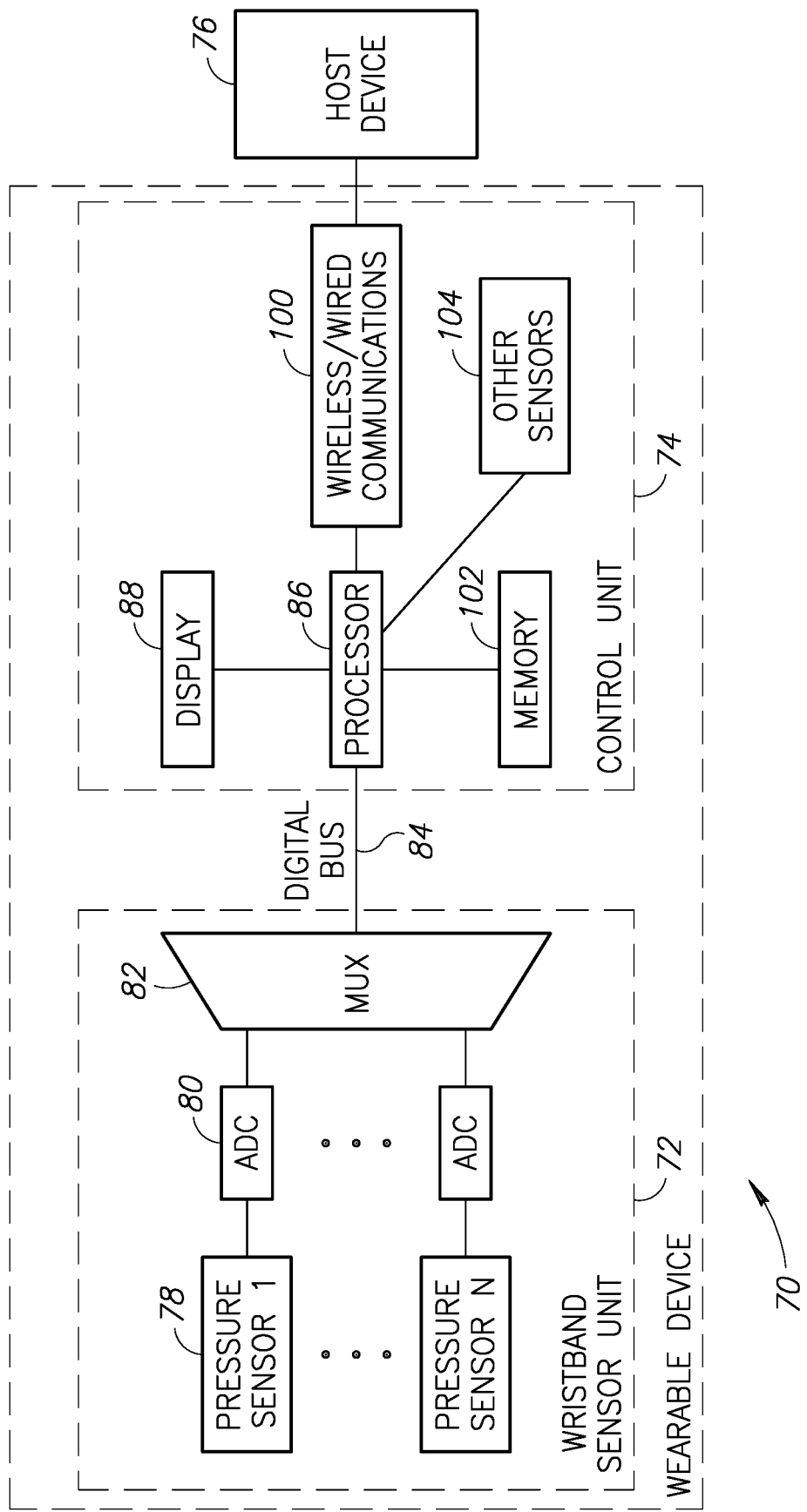
FIG. 6 is a block diagram illustrating an example wearable device constructed in accordance with the present invention.

A block diagram illustrating an example wearable device constructed in accordance with the present invention is shown in FIG. 6. The wearable device, generally referenced 70, comprises a wrist band sensor unit 72 and control unit 74 in communication with each other by digital bus 84. Wrist band sensor unit 72 comprises a plurality of pressure sensors 1 through N 78, each coupled to an analog to digital converter 80. The outputs of the ADCs are input to a multiplexer 82 which is provisioned to transmit all the input signals multiplexed onto digital bus 84. In one embodiment, the signals output from all the sensors 78 are input to the control unit 74.

The control unit 74 comprises a processor 86, e.g., CPU, microcontroller, microprocessor, etc., display subsystem 88, memory 102, e.g., volatile, non-volatile, flash, etc., wireless and wired communications subsystem 100 and one or more other non-pressure sensors 104, e.g., optical, photo plethysmograph, temperature, etc. The control unit 74 communications with a host device 76 via wireless and/or wired communications channels such as wireless LAN, Bluetooth Low Energy (BLE), Universal Serial Bus (USB) connection, etc. The processor 86 is configured to transmit and receive data with the wrist band sensor unit via the digital bus 84. The display subsystem is configured to display blood pressure measurements.

Figure 7:
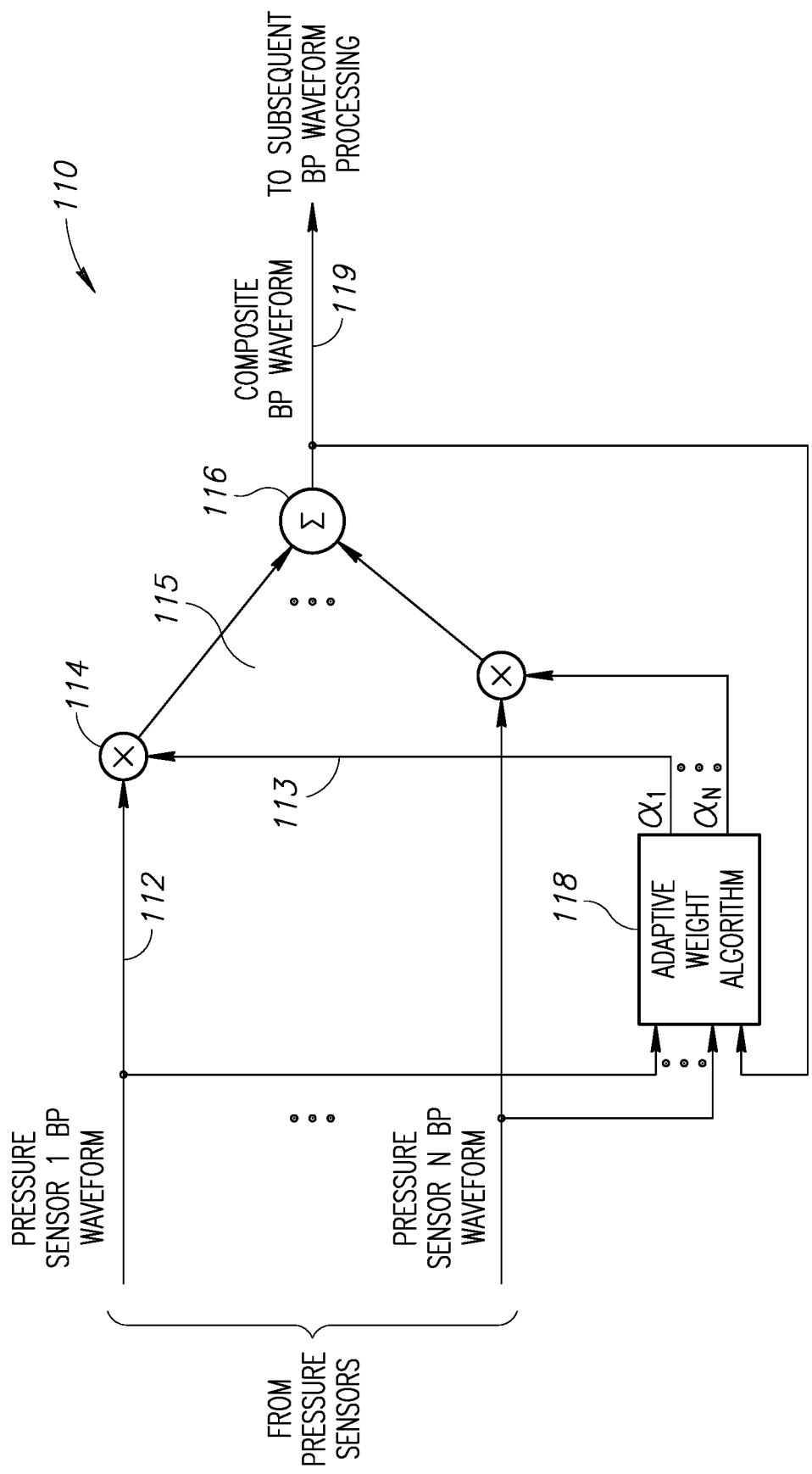
FIG. 7 is a block diagram illustrating an example circuit for generating a composite blood pressure waveform in accordance with the present invention.

A block diagram illustrating an example circuit for generating a composite blood pressure waveform in accordance with the present invention is shown in FIG. 7. The circuit, generally referenced 110, comprises an adaptive weight algorithm block 118, multipliers 1 through N 114 and summer 116. In operation, N scaling factors are applied to the blood pressure waveform data samples 112 received from N pressure sensors. The blood pressure waveform data is input to multipliers 114 as well as the adaptive weight algorithm block 118. The composite blood pressure waveform 119 is also input to the adaptive weight algorithm. The algorithm is operative to generate from the input data N scale factors 113 (i.e. coefficients) $\alpha_1$ through $\alpha_N$ which are respectively applied to the N multipliers 114. The products 115 generated by the multipliers are added via summer 116 to generate the composite blood pressure waveform 119 which is then further processed to generate blood pressure readings.

The adaptive weight algorithm 118, is configured to accept the N blood pressure waveform signals as well as the composite output waveform 119 and to estimate coefficients $\alpha_1$ through $\alpha_N$ such that the SNR on the composite blood pressure waveform 119 is maximized.

In an example embodiment, the weights are calculated via block 147 based on a Least Squares Maximum Ratio Combining (MRC) technique according to the following equations:

$$\hat{y} = \sum_{i=0}^{N} \alpha_i x_1 \quad (1)$$

$$\alpha_i = \frac{\hat{A}_i}{\sum_{k=1}^{N} \hat{A}_k^2} \quad (2)$$

where:
$\hat{y}$ is the output estimated blood pressure waveform signal;
$\alpha_i$ is the weight associated with the signal acquired from the $i^{th}$ pressure sensor;
$x_i$ is the signal acquired from the $i^{th}$ pressure sensor;
$\hat{A}_i$ is the estimate amplitude of $x_i$;

In one embodiment, the amplitudes of the signals can be estimated using any suitable well-known technique such as Root Mean Square estimation (RMS), Variance, etc.

Figure 8:
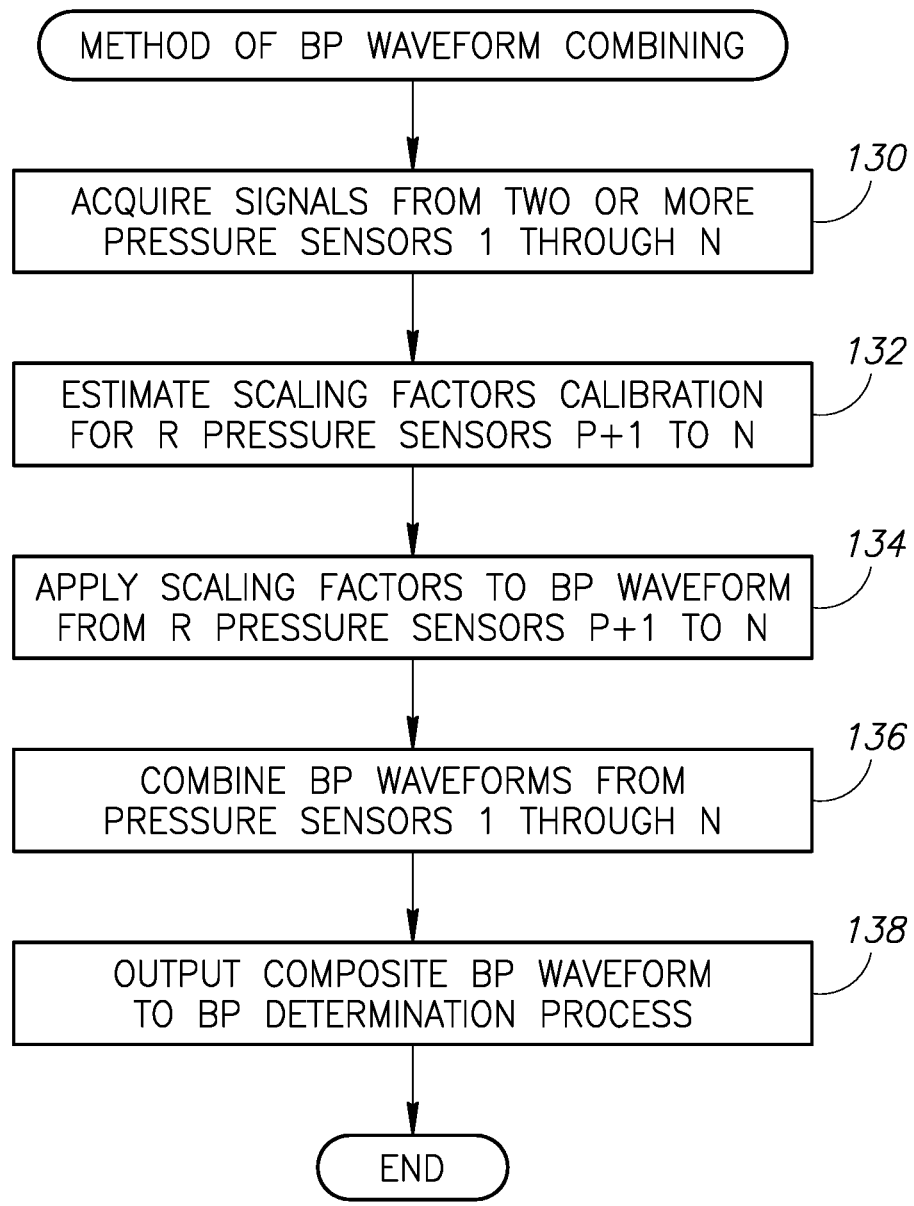
FIG. 8 is a flow diagram illustrating an example method of blood pressure waveform combining in accordance with the present invention.

A flow diagram illustrating an example method of blood pressure waveform combining (or calibration) in accordance with the present invention is shown in FIG. 8. Note that in this example method, a portion P of the N sensors are of higher accuracy (e.g., resistive MEMS type pressure sensors) while a portion R of the N sensors are of lesser accuracy (e.g., capacitive MEMS type pressure sensors), where R+P=N. Sensors 1 through P are higher accuracy sensors and sensors P+1 through N are lower accuracy sensors.

Referring to FIG. 8, first, the signals from a plurality of N pressure sensors are acquired (step 130). The scaling factors calibration for the blood pressure waveforms from R pressure sensors P+1 through N are then estimated (step 132). The blood pressure waveforms from R pressure sensors P+1 to N are multiplied by the estimated scaling factors obtained in step 132 (step 134). The scaled blood pressure waveforms obtained from sensors 1 through N are then combined (step 136) and a composite blood pressure waveform is output for further processing and to derive blood pressure readings from (step 138). The method yields a composite blood pressure waveform having a higher SNR.

Figure 9:
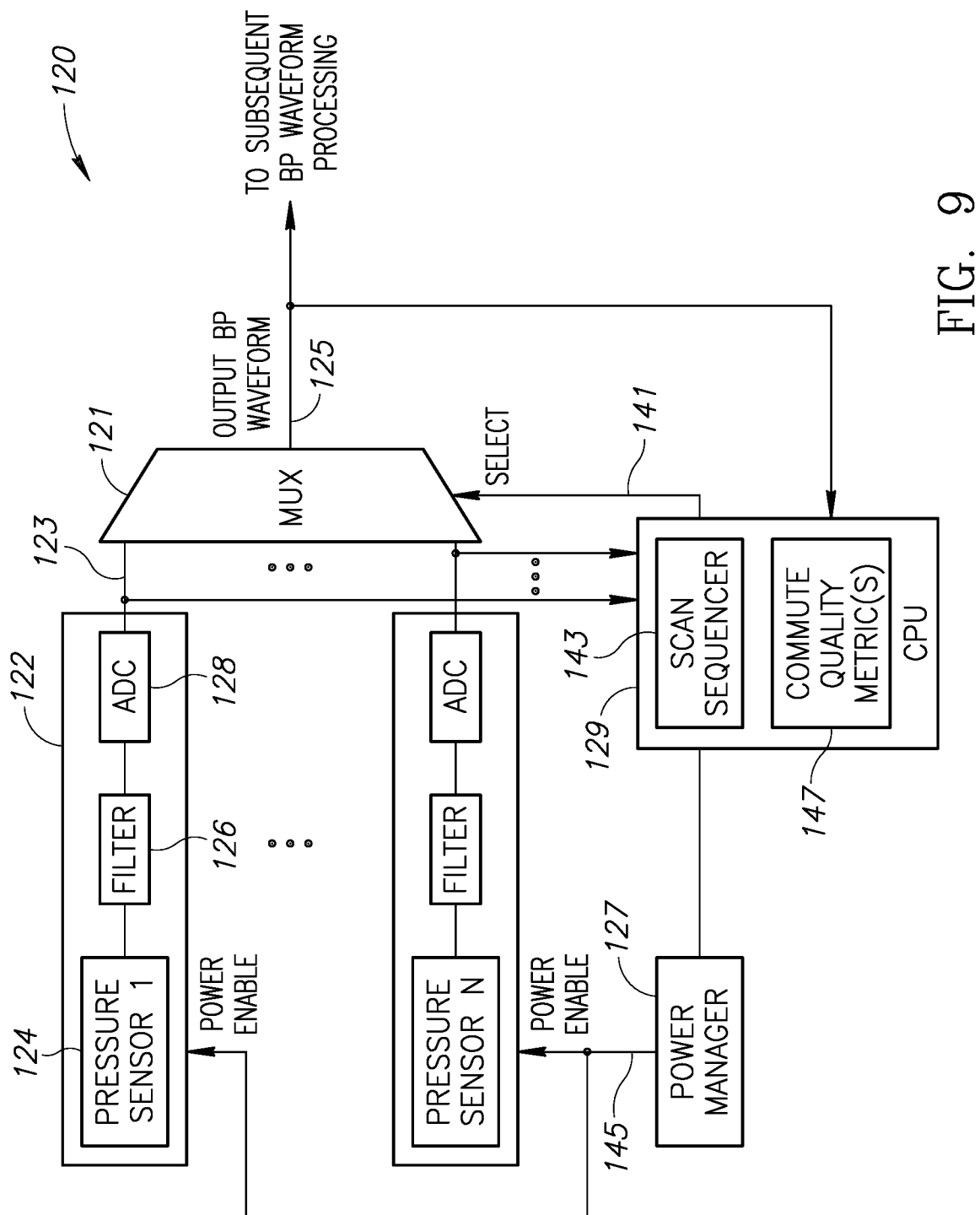
FIG. 9 is a block diagram illustrating an example circuit for selecting a blood pressure waveform from one of a plurality of pressure sensors in accordance with the present invention.

A block diagram illustrating an example circuit for selecting a blood pressure waveform from one of a plurality of pressure sensors in accordance with the present invention is shown in FIG. 9. The circuit, generally referenced 120, comprises a plurality N of pressure sensor input modules 122, multiplexer 121, power management unit 127, and processor block 129. Each pressure sensor input module 122 comprises pressure sensor 124, optional filter circuit 126, and analog to digital converter (ADC) 128. The processor 129 comprises, inter alia, scan sequencer 143 and quality metric(s) computation block 147.

As described supra, in one embodiment, the wearable device maximizes one or more quality metrics by selecting the signal output by a single pressure sensors and ignoring the signals from all other sensors. This can be achieved using software via the processor 86 (FIG. 6) whereby the signal waveforms from all sensors are received and all but one are discarded.

In this embodiment 120, power consumption is reduced by disabling power to all but one pressure sensor input module. In operation, signals from all N sensor input modules are input to the processor and one or more quality metrics are calculated via block 147. The scan sequencer controls the gathering of signal data from the N sensor input modules. In accordance with the calculated metrics, one of the sensor input modules is selected based on the leading metric.

Once a sensor input module is selected, the power to the N−1 non-selected sensor input modules is disabled via power enable signals 145 generated by power management block 127. The processor also generates the appropriate select command 141 to the multiplexer 121 to pass the signal generated by the selected sensor input module. The blood pressure waveform 125 output from the multiplexor is then processed further to generate a blood pressure reading. In one embodiment, data from all N pressure sensors can be re-evaluated (i.e. re-scanned) and a new sensor selected. The re-evaluation can be performed on a periodic basis, e.g., every ten seconds, or on a dynamic basis whereby scanning is initiated when some metric calculated from the sensor data falls below a threshold, e.g., sensor output falls below a certain SNR or RSSI.

It is noted that the one or more quality metrics computed by processor block 147 may comprise any desired metric. Example metrics include SNR and RSSI. It is appreciated, however, that the invention is not limited to these metrics.

Figure 10:
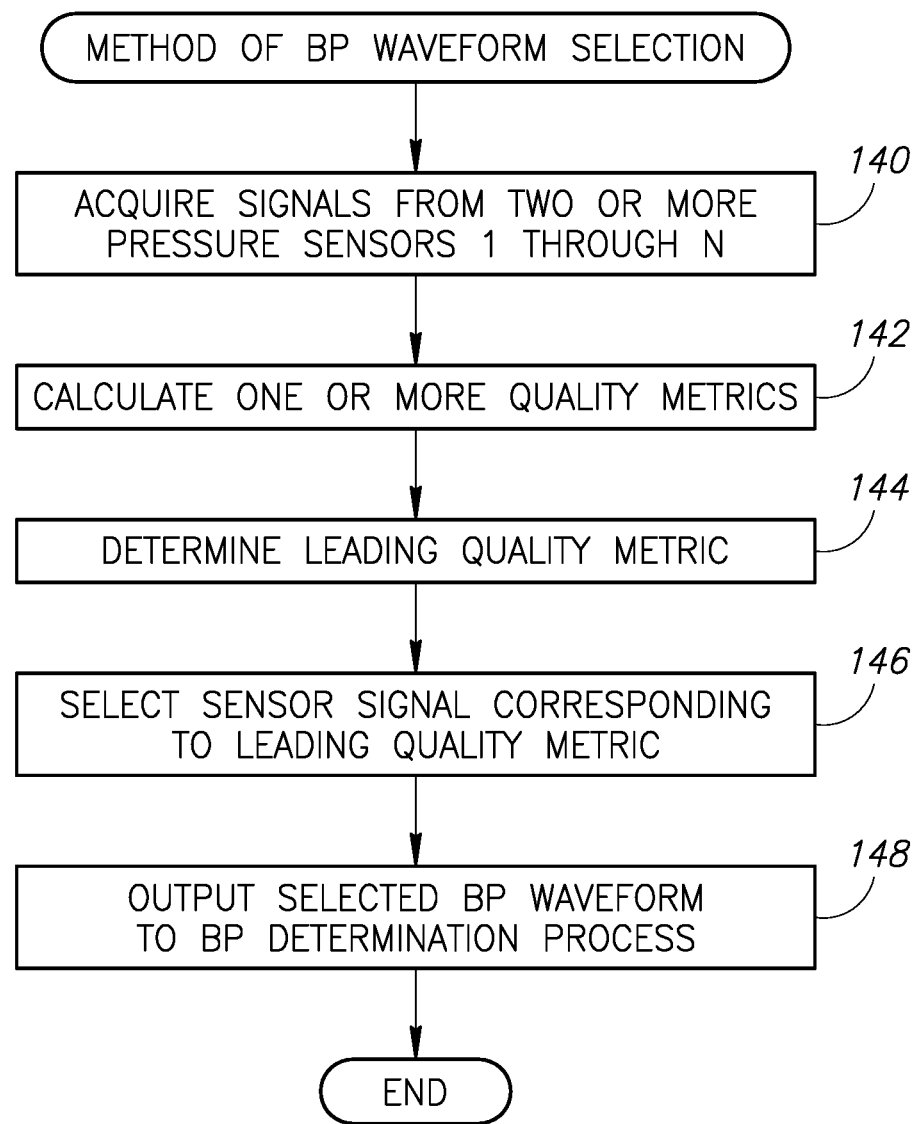
FIG. 10 is a flow diagram illustrating an example method of blood pressure waveform selection in accordance with the present invention.

A flow diagram illustrating an example method of blood pressure waveform selection in accordance with the present invention is shown in FIG. 10. First, the signals from a plurality of N pressure sensors are acquired and input to the processor (step 140). One or more quality metrics (e.g., SNR, RSSI, etc.) are calculated (step 142). The metric calculations are compared and the leading metric is determined (step 144). The sensor signal corresponding to the leading quality metric is then selected (step 146). The selected blood pressure waveform is output to the blood pressure determination process (step 148). Optionally, to reduce power consumption, power to the sensor input modules corresponding to the non-selected sensor are disabled. As described supra, data from all N pressure sensors can be rescanned and a new sensor selected.

Those skilled in the art will recognize that the boundaries between logic and circuit blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediary components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation. A single operation may be distributed in additional operations and operations may be executed at least partially overlapping in time. Moreover, alternative embodiments may include multiple instances of a particular operation, and the order of operations may be altered in various other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the claims, any reference signs placed between parentheses shall not be construed as limiting the claim. The use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first," "second," etc. are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A computerized method of generating an output blood pressure (BP) signal, comprising:
   providing a plurality of N pressure sensors;
   acquiring a plurality of N blood pressure waveform signals, each waveform signal acquired from one of said pressure sensors; and
   combining, via a processor, said N blood pressure waveform signals, by applying weighted coefficients to each of said N blood pressure waveforms, to generate said output blood pressure signal therefrom, said output blood pressure signal comprised of a weighted sum of each of said N blood pressure waveforms.

2. The method according to claim 1 further comprising deriving at least one of a systolic and diastolic blood pressure measurement from said output blood pressure signal.

3. The method according to claim 1, wherein said plurality of N pressure sensors are adapted to sense blood pressure from at least one of said radial, ulnar and brachial arteries.

4. The method according to claim 1, wherein said output blood pressure signal has a higher signal quality metrics than a signal quality metrics of each of the N blood pressure waveform signals acquired from said N pressure sensors signals.

5. A computerized method of obtaining an output blood pressure (BP) signal, comprising:
   providing a plurality of N pressure sensors;
   acquiring a plurality of N blood pressure waveform signals, each waveform signal acquired from one of said pressure sensors; and
   selecting, via a processor, one of said N blood pressure waveform signals from one of said plurality of N pressure sensors in accordance with one or more quality metrics as said output blood pressure signal;
   wherein non-selected pressure sensors and their related circuitry are powered down to reduce power consumption.

6. The method according to claim 5, wherein said one or more quality metrics is selected from a group comprising signal to noise ratio (SNR) and received signal strength indication (RSSI).

7. A computerized method of generating an output blood pressure (BP) signal, comprising:
   providing a plurality of N pressure sensors;
   acquiring a plurality of N blood pressure waveform signals, each waveform signal acquired from one of said pressure sensors;
   utilizing waveform signals from one or more relatively accurate pressure sensors from among said plurality of pressure sensors to calibrate one or more less accurate pressure sensors within said plurality of pressure sensors; and combining, via a processor, said N blood pressure waveform signals including one or more calibrated blood pressure waveform signals to generate a composite output blood pressure signal therefrom.

8. The method according to claim 7, wherein said combining comprises calculating a higher signal to noise ratio (SNR) composite blood pressure signal.

9. The method according to claim 7, wherein said composite blood pressure signal comprises a weighted sum utilizing coefficients for each of said N blood pressure waveforms.

10. The method according to claim 9, wherein said coefficients are estimated using an adaptive algorithm such that said composite output blood pressure signal has a higher signal to noise ratio (SNR) than one or more of said N pressure sensor signals.

11. The method according to claim 7, wherein said calibrating one or more less accurate pressure sensors comprises:

estimating scale factors for said one or more less accurate pressure sensors from said one or more relatively accurate pressure sensors; and multiplying blood pressure waveform signals from said one or more less accurate pressure sensors by said scale factors to generate said one or more calibrated blood pressure waveform signals.

12. The method of claim 7, wherein said output blood pressure signal has a higher signal quality metrics than a signal quality metrics of each of the N blood pressure waveform signals acquired from said N pressure sensors signals.

13. A computerized method of obtaining an output blood pressure (BP) signal, comprising:

providing a plurality of N pressure sensors;

acquiring a plurality of N blood pressure waveform signals, each waveform signal acquired from one of said pressure sensors;

calibrating, via a processor, one or more less accurate pressure sensors within said plurality of pressure sensors using waveform signals from one or more relatively accurate pressure sensors;

selecting one of said N blood pressure waveform signals from the one or more less accurate pressure sensors in accordance with one or more quality metrics; and outputting said selected signal as said output blood pressure signal.

14. The method according to claim 13, wherein said one or more quality metrics is selected from a group comprising signal to noise ratio (SNR) and received signal strength indication (RSSI).

15. The method according to claim 13, wherein said non-selected pressure sensors and their related circuitry are powered down to reduce power consumption.

16. The method according to claim 13, wherein said plurality of N pressure sensors are adapted to sense blood pressure from at least one of said radial, ulnar and brachial arteries.

17. The method according to claim 13, wherein said calibrating one or more less accurate pressure sensors comprises:

estimating scale factors for said one or more less accurate pressure sensors from said one or more relatively accurate pressure sensors; and multiplying blood pressure waveform signals from said one or more less accurate pressure sensors by said scale factors to generate said one or more calibrated blood pressure waveform signals.

18. An apparatus for generating an output blood pressure (BP) signal, comprising:

a plurality of N pressure sensors;

an acquisition circuit operative to acquire a plurality of N blood pressure waveform signals, each waveform signal acquired from one of said pressure sensors;

a processor, said processor configured to execute program instructions to:

utilize waveform signals from one or more relatively accurate pressure sensors from among said plurality of pressure sensors to calibrate one or more less accurate pressure sensors within said plurality of pressure sensors; and combine said N blood pressure waveform signals including one or more calibrated blood pressure waveform signals to generate said composite output blood pressure signal therefrom.

19. The apparatus according to claim 18, wherein said combining comprises calculating a higher signal to noise ratio (SNR) composite blood pressure signal.

20. The apparatus according to claim 18, wherein said composite blood pressure signal comprises a weighted sum utilizing coefficients for each of said N blood pressure waveforms.

21. The apparatus according to claim 20, wherein said coefficients are estimated using an adaptive algorithm such that said composite output blood pressure signal has a higher signal to noise ratio (SNR) than one or more of said N pressure sensor signals.

22. The apparatus according to claim 18, wherein said plurality of N pressure sensors are adapted to sense blood pressure from at least one of said radial, ulnar and brachial arteries.

23. The apparatus according to claim 18, wherein said calibrating one or more less accurate pressure sensors comprises:

estimating scale factors for said one or more less accurate pressure sensors from said one or more relatively accurate pressure sensors; and multiplying blood pressure waveform signals from said one or more less accurate pressure sensors by said scale factors to generate said one or more calibrated blood pressure waveform signals.

24. An apparatus for generating an output blood pressure (BP) signal, comprising:

a plurality of N pressure sensors;

an acquisition circuit operative to acquire a plurality of N blood pressure waveform signals, each waveform signal acquired from one of said pressure sensors;

a processor, said processor configured to execute program instructions to:

utilize waveform signals from one or more relatively accurate pressure sensors from among said plurality of pressure sensors to calibrate one or more less accurate pressure sensors within said plurality of pressure sensors;

select one of said N blood pressure waveform signals in accordance with one or more quality metrics; and output said selected signal as said output blood pressure signal.

25. The apparatus according to claim 24, wherein said one or more quality metrics is selected from a group comprising signal to noise ratio (SNR) and received signal strength indication (RSSI).

26. The apparatus according to claim 24, wherein said non-selected pressure sensors and their related circuitry are powered down to reduce power consumption.

27. The apparatus according to claim 24, wherein said plurality of N pressure sensors are adapted to sense blood pressure from at least one of said radial, ulnar and brachial arteries.

28. The apparatus of claim 24, wherein the blood pressure signal has a higher signal quality metrics than a signal quality metrics of the N blood pressure waveform signals acquired from said N pressure sensors signals to thereby result in enhanced accuracy of the obtained output blood pressure signal.

* * * * *